US009255156B2

(12) United States Patent
Nativi et al.

(10) Patent No.: US 9,255,156 B2
(45) Date of Patent: Feb. 9, 2016

(54) IMMUNOGENIC SYNTHETIC GLYCOCONJUGATE FOR THE IMMUNOTHERAPY OF MELANOMA (71) Applicants: Cristina Nativi, Florence (IT); Lucio Toma, Voghera (IT); Barbara Richichi, Sesto Fiorentino (IT); Carlotta Lunghi, Montale (IT)

(72) Inventors: Cristina Nativi, Florence (IT); Lucio Toma, Voghera (IT); Barbara Richichi, Sesto Fiorentino (IT); Carlotta Lunghi, Montale (IT)

(73) Assignee: Azienda Ospedaliero-Universitaria Careggi, Florence (IT)

( * ) Notice: Subject to any disclaimer, the term of this patent is extended or adjusted under 35 U.S.C. 154(b) by 0 days.

(21) Appl. No.: 14/183,072

(22) Filed: Feb. 18, 2014

(65) Prior Publication Data

US 2014/0161806 A1 Jun. 12, 2014

Related U.S. Application Data (62) Division of application No. 13/505,844, filed as application No. PCT/IB2010/055003 on Nov. 4, 2010, now Pat. No. 8,680,043.

(30) Foreign Application Priority Data

Nov. 4, 2009 (IT) .................. FI2009A0230

(51) Int. Cl.
*A61K 38/00* (2006.01)
*C07K 16/44* (2006.01)
*A61K 47/48* (2006.01)

(52) U.S. Cl.
CPC .............. *C07K 16/44* (2013.01); *A61K 47/4833* (2013.01); *A61K 47/48092* (2013.01); *A61K 47/48284* (2013.01)

(58) Field of Classification Search
CPC .............. A61K 38/00; A61K 39/0011; A61K 39/39558; A61K 39/395
See application file for complete search history.

(56) References Cited

U.S. PATENT DOCUMENTS

2006/0093610 A1 * 5/2006 Lang et al. .................. 424/170.1

OTHER PUBLICATIONS

Monoclonal Antibody Production, A Report of the Committee on Methods of Producing Monoclonal Antibodies Institute for Laboratory Animal Research National Research Council, 1999.*
International Search Report and Written Opinion dated Apr. 6, 2011 corresponding to International Patent Application No. PCT/IB2010/055003.
Ristori, S., et al., "Structural study of liposomes loaded with GM3 lactone analogue for the targeting of tumor epitopes;" Biochimica et Biophysica Acta, 1788, 2009, pp. 2518-2525.
Toma, L., et al., "Synthesis, Conformational Studies, Binding Assessment and Liposome Insertion of a Thioether-Bridged Mimetic of the Antigen GM3 Ganglioside Lactone;" Chembiochem, vol. 8, Sep. 2007, XP-002579807, pp. 1646-1649.
"Preparation of Hapten-Carrier Immunogen Conjugates;" In G. T. Hermanson: "Bioconjugate Techniques," Jan. 1995, Academic Press, San Diego, XP-002627387, pp. 419-429.

* cited by examiner

*Primary Examiner* — Marcela M Cordero Garcia
*Assistant Examiner* — Kaipeen Yang
(74) *Attorney, Agent, or Firm* — Ohlandt, Greeley, Ruggiero & Perle, L.L.P.

(57) ABSTRACT

A specific antibody against a compound of formula (I)

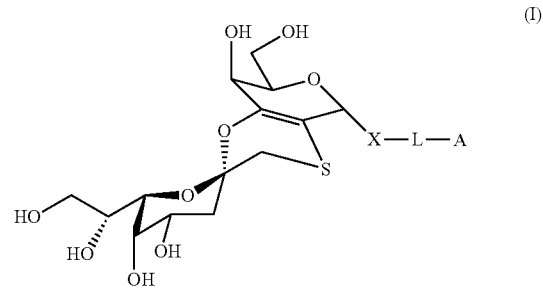

wherein X is O, NH, S, $CH_2$; L is a linker that is a divalent spacer; A is an adjuvant or carrier that is an immunogenic molecule or an immunogenic particle; and wherein bonds between linker and saccharide moiety and between linker and carrier are of covalent type; wherein the linker L presents a chemical structure suitable to space the saccharide moiety and the carrier by 7-30 atoms when the adjuvant/carrier A is a biomacromolecule or by 19-30 atoms when the adjuvant/carrier A is a metallic nanoparticle; wherein the carrier/adjuvant A can be selected among a macromolecule, a macrocycle, a dendrimer, a liposome, a nanoparticle, an oligosaccharide featuring from two to five monosaccharidic units or cells like dendritic cells.

6 Claims, 3 Drawing Sheets

ISOTYPE TEST

IMMUNOGENIC SYNTHETIC GLYCOCONJUGATE FOR THE IMMUNOTHERAPY OF MELANOMA

CROSS-REFERENCED APPLICATIONS

This application is a divisional application of U.S. patent application Ser. No. 13/505,844, filed on Jun. 26, 2012, which is the National Stage of International Application No. PCT/IB2010/055003, filed on Nov. 4, 2010, which claims benefit of Italian Patent Application No. FI2009A000230, filed on Nov. 4, 2009, all of which are incorporated herein by reference in their entireties.

FIELD OF THE DISCLOSURE

The disclosure relates to the synthetic chemistry domain and in particular the synthesis of immunogenic glycoconjugate derivatives, their synthetic methods and their use for active and passive immunotherapy or for the prognosis of cancers characterized by the overexpression of $GM_3$ ganglioside and $GM_3$ lactone.

STATE OF THE ART

Figure 1:
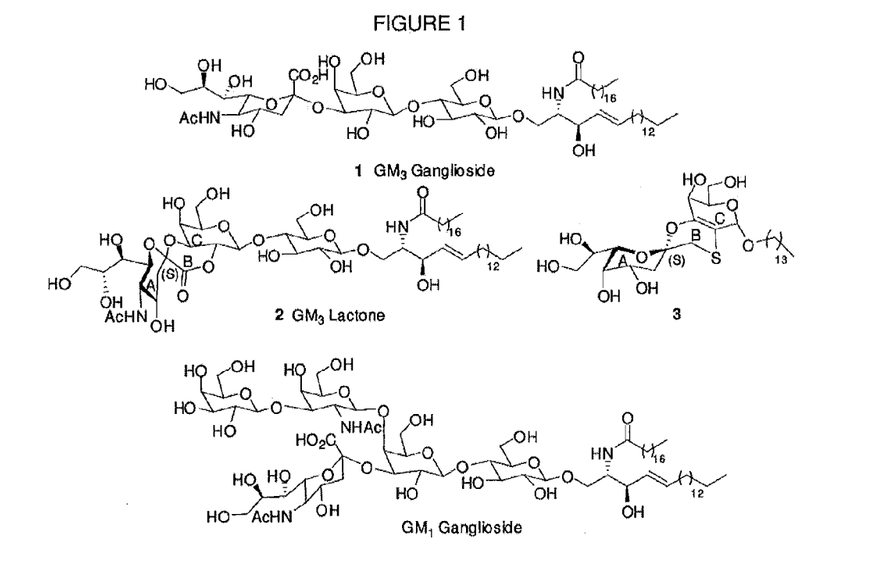
FIG. 1—Structure of the $GM_3$ ganglioside 1, $GM_3$ lactone 2, thioether mimetic 3 and $GM_1$.

Immunotherapy against tumours and against melanoma in particular has a long history but only recently this therapeutic approach has found a reliable scientific rationale. The main target of this biological therapy consists of teaching the tumour bearing host's immune system how to recognize antigens express on tumoral cells and destroy them, without damaging healthy cells. The success of this therapy greatly depends on the choice of the antigens responsible for the growth and proliferation of the tumour. $GM_3$ ganglioside 1 (FIG. 1), a glycosphingolipid found in essentially all types of mammalians' cells and tissues, is the major ganglioside in normal melanocytes. Ganglioside 1 and especially its metabolite, the $GM_3$ lactone 2 (FIG. 1), are overexpressed in melanoma cells with metastatic potential. These antigens are wrongly recognized as "self" by patient's immune system and are potential targets for the immunotherapy of this tumours. Although more immunogenic than $GM_3$ ganglioside 1, $GM_3$ lactone 2 failed as immunostimulant because unstable under physiological conditions, in unsuitable to be used in immunotherapy as melanoma's associate antigen. Toma et al. *ChemBioChem,* 2007, 8, 1646 describes the rational design and the synthesis of the hydrolytically stable mimetic 3 (FIG. 1) which is remarkably simpler than the native 2. The mimetic 3, as reported after its publication, has been demonstrated to be scarcely immunogen. Aim of the present disclosure is to provide a synthetic derivative of $GM_3$ lactone which is hydrolytically stable under physiological conditions and good to raise the immune system to elicit antibodies able to recognize antigens express on tumoral cells which present overexpression of GM3 lactone (i.e. melanoma cells or colon tumoral cells).

DESCRIPTION AND SHORTENING

KLH: Keyhole Limpet Hemocyanin
CRM: Cross-Reacting Material 197 (non toxic mutation of difteric toxin)
OMP: Outer Membrane Protein
BSA: Bovine Serum Albumin
cBSA: cationized Bovine Serum Albumin
HSA: Human Serum Albumin
BCG Bacillus Calmette and Guerin
MPL: Membrane-Patched Proteoliposomes
MDP: Muramyl DiPeptide
Pal3CysSer: N-α-palmitoyl-S-[2,3-bis(palmitoyloxy)-(2RS)-propyl]-Cys-Ser-OH
Pal3Cys: N-α-palmitoyl-S-[2,3-bis(palmitoyloxy)-(2RS)-propyl]-L-cysteine
QS-21: Quillaja Saponaria Molina based immunological adjuvant
CpG: Cytosine linked to a Guanine by a phosphate bond
RAFT: Regioselectively Addressable Functional Template
ODN: OligoDeoxyNucleotides

SUMMARY

A specific antibody against a compound of formula (I)

wherein
  X is O, NH, S, $CH_2$;
  L is a linker that is a divalent spacer;
  A is an adjuvant or carrier that is an immunogenic molecule or an immunogenic particle; and
  wherein bonds between linker and saccharide moiety and between linker and carrier are of covalent type;
  wherein the linker L presents a chemical structure suitable to space the saccharide moiety and the carrier by 7-30 atoms when the adjuvant/carrier A is a biomacromolecule or by 19-30 atoms when the adjuvant/carrier A is a metallic nanoparticle; and
  wherein said carrier/adjuvant A can be selected among a macromolecule, a macrocycle, a dendrimer, a liposome, a nanoparticle, an oligosaccharide featuring from two to five monosaccharidic units or cells like dendritic cells.

The antibody obtainable by immunization of experimental animal of murine genus by administration of said compound of formula (I).

A method comprising administering a specific antibody against a compound of formula (I) as a medicament to a patient in need thereof.

A method comprising administering the specific antibody to a patient in need of treatment and/or prevention of tumors whose cells hyper-express GM-3 ganglioside and/or GM-3 lactone.

A method comprising the use of the specific antibodies as a tool for diagnosis and/or prognosis of tumors whose cells hyper-express GM-3 ganglioside and/or GM-3 lactone.

A pharmaceutical composition containing at least specific antibody against a compound of formula (I) and at least another pharmaceutically acceptable ingredient.

DETAILED DESCRIPTION OF THE PREFERRED EMBODIMENT

In the scope of the present disclosure, the linker L is a divalent spacer with a structure suitable for maintaining a correct distance between the carbohydratic portion and the carrier/adjuvant avoiding the undesired masking of their antigenic regions: as first choice the linker presents a chemical structure suitable to space the carbohydratic portion and the carrier by 7-30 atoms or better by 12-16 atoms when the adjuvant/carrier A is a biomacromolecule or by 19-30 atoms when the adjuvant/carrier A is a metallic nanoparticle.

In the scope of the present disclosure, the adjuvant/carrier A is an immunogenic species i.e. able to induce an immune response when administered to an animal subject; the latter carrier/adjuvant A can be selected among a macromolecule, a macrocycle, a dendrimer, a liposome, a nanoparticle, an oligosaccharide featuring from two to five monosaccharidic units or cells like dendritic cells (DC).

Macromolecule means a molecule containing at least 100 atoms, among these are included the bio-macromolecules like proteins, lipids and polysaccharides.

Macrocycles means compound featuring a seven- (or larger-) membered ring like calixarenes, phthalocyanines, cyclodestrins, porfirines and cyclo-oligopepides.

Dendrimers of G0, G1 and G2 are included. PAMAM (polyethylenamine) is a good example of dendrimer.

Nanoparticles are particles whose dimensions range between 1 and 100 nm; they are formed by metals or metal oxides selected among Au, Fe, Ti.

Optionally, if A is a carrier with a modest immunogenicity a compound of formula (I) can be associated with another suitable adjuvant able to increase the immunogenicity of the carrier. In this case object of the disclosure is a composition comprising a compound of formula (I) as above described and another adjuvant B able to enhance the immunogenity of carrier A.

Preferably, the carrier/adjuvant A and B is selected in the group consisting of KLH, CRM, OMP, BSA, HAS, BCG, MLP, MDP, Pal3CysSer, Pal3Cys, QS21, trealosio-6,6'-dimicolato, synthetic CpG, CpG-DNA, Nisseria

Meningitis, tetanic toxin, bacterial toxin, liposome, gold nanoparticles, Fe(II) oxide nanoparticles, calixarenes, dendrimers, RAFT, DC, as single species or combined.

When the carrier/adjuvant is proteic the linkage between linker and carrier/adjuvant is chosen in the group of amidic, aminic, iminic, ethereal, thioethereal, disulfide, ester, thioester, phosphate, phosphonate, ureidic, thioureidic, carbamate, carbonate, where at least one atom belongs to the protein.

When the carrier A is a nanoparticles the linker is bond to the nanoparticles with a pseudo-covalent linkage though a sulfur atom or a disulfide group.

When A is a protein the linker presents in preference the structure R1—Z—W1—R2—W2 where R1 and R2 independently from each other are a C2-C8- alkyl, C2-C8-alkenyl, C5-C7-cycloalkyl, 1-4-phenyl; Z is O, S, NH; W1 is missing, C═O, C═NH, S; W2 is missing, C═O, C═NH, S, 1,4-succinamide. The above reported alkyls are in preference linear.

Examples of possible linkers are:

More preferred are those compounds wherein:
X=O;
A is a protein;
L is a bivalent spacer of structure (CH2)n-NH—CO—(CH2)m-CO—Y where n and/or m are integer ranging from 2 to 8 and Y is an NH which is part of A.

Figure 2:
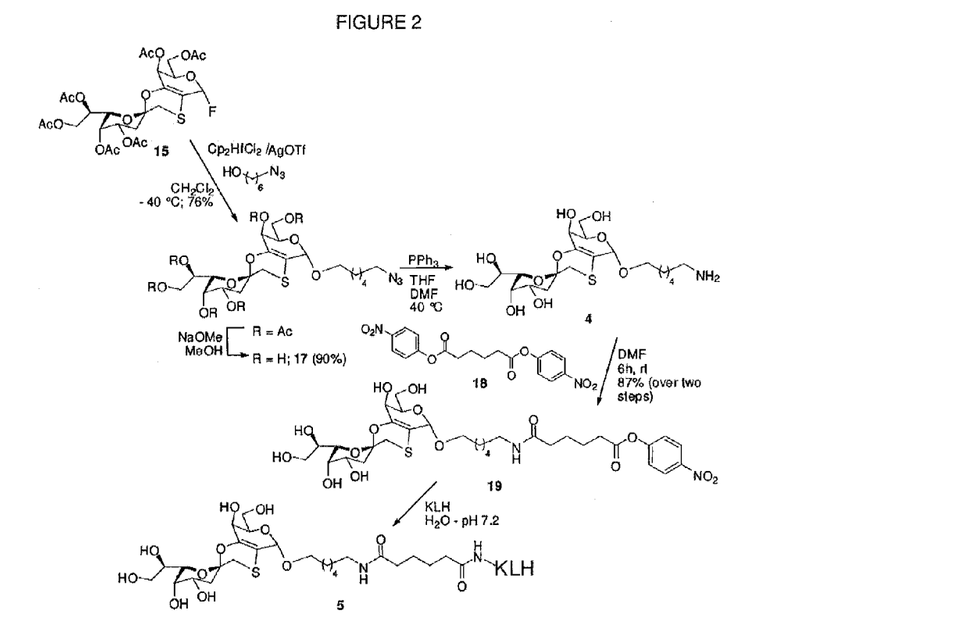
FIG. 2—Synthesis of a glycoconjugate of formula (I) according to the disclosure, in particular of compound 5 KLH-conjugate.

A preferred compound is the compound 5 (FIG. 2) of structure (I) where X is O, linker L is —(CH2)6NHCO—(CH2)4-CO— and carrier A is KLH linked through lysine —NH2 residues to —COOH residues of the linker.

Compounds of formula (I) as above described can be obtained starting from compounds of structure where:
G is F, Br or Cl; SR, SAr or trichloroacetimide, phosphate where R is Et or C1-C4 alkyl; Ar is Ph, substituted Ph, Pyridine, chinoline or other aromatic heterocycles;
P independently are suitable hydroxyls protecting groups selected among those protecting groups known to those skilled in the art and such as and preferably acetyl, benzoyl, silyl and benzyl; prepared by known synthetic methods for the insertion of a linker L or L-A.

In a preferred embodiment a compound of formula (II) has groups P all the same.

In the event a compound of formula (II) as above described is coupled to the linker only it will follow, after optional suitable deprotection of hydroxyl groups, coupling, through known synthetic strategies, with a carrier/adjuvant A.

In a particular, as example embodiment, is herein reported (FIG. 2) the synthetic scheme for the compound 5 obtained from the compound 15, i.e. a compound of formula (II) where G is F. The compound 15 was prepared as already reported in Toma et al. *ChemBioChem*, 2007, 8, 1646. The ω-amino glicosyl derivative 4 (FIG. 2) was prepared from the fluoro derivative 15 by treatment with azido hexanol under Ley's glycosylation conditions. The pseudo-α azido derivative 17 obtained after removal of acetyl groups, was reduced under Staudinger's reaction conditions to give 4 which was reacted with the bis-p nitrophenyl adipic ester 18 (Wu, X., Ling, C.-C., Bundle, D. *Org. Lett.* 2004, 6, 4407) to form the activated carboxylic derivative 19 (87% over two steps) (Scheme 3). Finally, 19 was conjugated to the proteic carrier KLH. The KLH-thioether conjugate 5 was prepared by mixing 19 with KLH (phosphate buffer, room temperature, 20 h). Saccharide molecule/KLH loading was determined by trinitrobenzensulfonic (TNBS) test (Habeeb, F.S.A. *Anal. Biochem.* 1966, 14, 328) to be ~27%.

Compounds of formula (I) as above described are artificial antigens, mimetic of the $GM_3$ lactone and therefore useful as active ingredient for vaccines against tumoral cells over-expressing $GM_3$ ganglioside and $GM_3$ lactone, in particular they are useful in the treatment and/or the prevention and/or the diagnosis of melanoma and cancers of colon.

Compounds of formula (I) as above described can also be useful as diagnostic devices for tumors whose cells over-express $GM_3$ ganglioside and $GM_3$ lactone.

Surprisingly indeed, the compound in the embodiment 5, when is administrated to mice, produced a strong immune response and the antibodies obtained are able to bind to the $GM_3$ ganglioside overexpressed on melanoma tumoral cells or colon tumoral cell lines.

Figure 3:
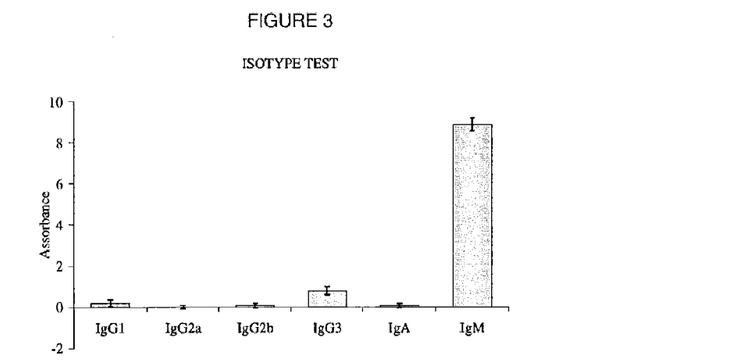
FIG. 3—ELISA tests performed for isotype determination. The hybridoma IV1:4C5C4 supernatant results to be composed of two isotypes: IgM and IgG3.

To determine the immunogenicity of the mimetic 5, BALB/c mice were immunized with the KLH conjugate. Following Milstein procedure (Galfrè, G., Milstein, C., "Preparation of monoclonal antibodies: strategies and procedures" in *Methods Enzymol.*, 73(Pt B), 3-46, (1981)) for the production of monoclonal antibodies, after sequential immunizations spleen cells from immunized mice were collected and fused with a hypoxanthine-aminopterin-thymidine (HAT) sensitive mouse myeloma cell line (NS0). The ensuing hybridomas were screened by testing supernatants for binding to $GM_3$ ganglioside 1 by enzyme-linked immunosorbent assay (ELISA). The supernatant displaying the highest absorbance (IV1:4C5C4) was then chosen for further analyses. An ELISA test aimed at isotype determination was also performed. The IV1:4C5C4 supernatant turned out to be composed by two isotypes: IgM and IgG3, with the IgM quantitatively prevailing on the IgG3 (FIG. 3).

Figure 4:
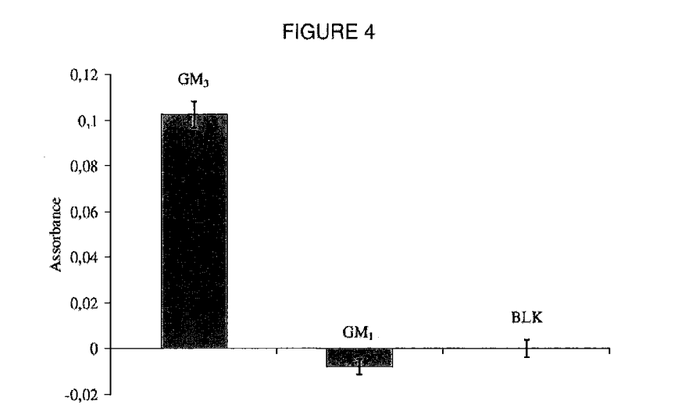
FIG. 4—ELISA test to compare antibody immunoreactivity towards either $GM_3$- or $GM_1$-ganglioside.
Figure 5:
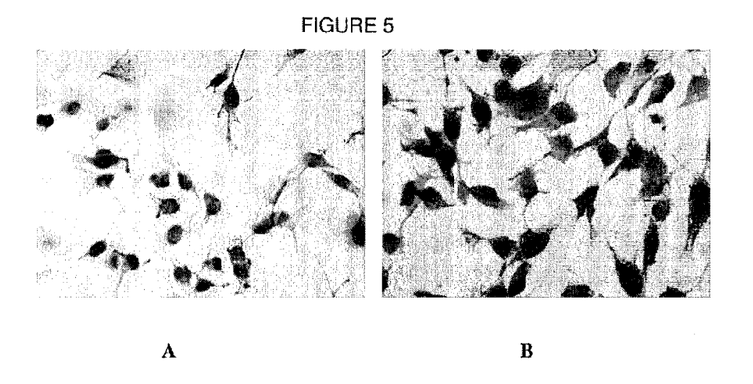
FIG. 5—Melanoma cell lines expressing (A375) and not expressing (WM-266-4) $GM_3$ antigen. Signals were obtained using hybridoma population IV1:4C5C4 supernatant.

The immunoreactivity of the IV1:4C5C4 supernatant towards either $GM_3$- or $GM_1$-ganglioside was then screened through an ELISA test. Results (FIG. 4) clearly indicated that the supernatant indeed binds $GM_3$ whereas no appreciable binding to $GM_S$ was observed. Finally, to evaluate the cross-reactivity of the polyclonal serum for $GM_3$ expressed on melanoma cells, immunocytochemistry with B16F1 melanoma cells treated with the hybridoma population IV1:4C5C4 supernatant was performed. Reference samples were treated with the commercially available anti-$GM_3$ monoclonal antibody (M2590) (positive control) and with an hybridoma supernatant resulted negative to the first ELISA test (taken as negative control). Results indicated a clear positivity of the cell line tested evidenced by the brown staining. Note that there is no detectable signal at the nuclear level but only at the cytoplasmatic membrane level. It is evident (FIG. 5) that the IV1:4C5C4 supernatant is able to recognize the $GM_3$ ganglioside and the $GM_3$ lactone expressed on melanoma cells better than the antibody anti-$GM_3$ M2590.

All together, data herein reported indicate that the glycoconjugate 5 is a real immunogen "in vivo" since it is capable to induce the formation of specific $GM_3$ antibodies. These antibodies cross react with the native antigen in ELISA tests as well as with melanoma cell lines.

Two main points must be considered: compounds of formula (I) as hereinabove described, and in particular the KLH-conjugate 5, overcomes the problem of the low immunogenicity typical of gangliosides and droops the immunotolerance generally preserved by the $GM_3$ ganglioside covalently linked to carriers such as the KLH (Bitton, R. J., et al. *Oncology Report* 2002, 9, 267; Gabri, M. R.; et al. *Clin. Cancer Res.* 2006, 12, 7092). These results prompt to further clonings of the IV1:4C5C4 hybridoma and purification of the IN/1:4C5C4 supernatant to obtain the monoclonal antibody anti $GM_3$ and $GM_3$ lactone to be used in the future for the passive immunotherapy of tumours whose cells overexpress GM3 ganglioside and GM3 ganglioside lactone, such as melanoma cells and colon tumour cell lines.

In addition the disclosure relates to specific antibodies against the artificial antigen of formula (I). For an aspect the present disclosure relates to hybridomas obtainable by immunization of mice with compounds of formula (I).

For another aspect the disclosure relates to chimeric or humanized antibodies including the variable or hyper variable sequences of the monoclonal antibodies achievable by immunization of mice with compounds of formula (I).

The above said antibodies can be useful active ingredient in pharmaceutical compositions for passive immunization in particular for the immunization against tumours whose cells overexpress GM3 ganglioside and GM3 lactone and in preferred embodiments are useful in the treatment of melanoma and colon cancers.

The above said antibodies can also be useful as diagnostic agents and/or prognostic of the above mentioned tumours.

The term "tumours whose cells overexpress $GM_3$ ganglioside and $GM_3$ lactone" as used herein means those tumours which analyzed by antigen-antibody (commercially available antibody anti-$GM_3$) and by immunocytochemical tests result to be positive to said overexpression.

The present disclosure could be better understood upon reading of the following preferred embodiments.

EXPERIMENTAL SECTION

Synthesis of compound 20

To a mixture of 15 (160 mg, 0.25 mmol), bis(cyclopentadienyl)hafnium(IV) dichloride ($Cp_2HfCl_2$) (170 mg, 0.45 mmol), AgOTf (250 mg, 0.97 mmol) and 6-azido-1-hexanol (70 mg, 0.5 mmol) cooled to −40° C., dry $CH_2Cl_2$ (30 mL) was added. After 40 min at −40° C. the solution was neutralized with $NEt_3$ and filtered through a pad of Celite® and the filtrate was washed with a saturated solution of $NaHCO_3$ (1×50 mL) then with brine (1×50 mL). The organic phase was dried over $Na_2SO_4$ and concentrated to dryness to give 200 mg of crude. The crude was purified by flash column chromatography on silica gel (petroleum ether/EtOAc 1:1) to give 20 (150 mg, 80%), as a glassy solid. $^1$H NMR (400 MHz, $CDCl_3$): δ 5.37 (d, 1H, $J_{d-e}$=2.4 Hz), 5.32 (bs, 1H), 5.26-5.21 (m, 1H), 5.12-5.09 (m,1H), 4.97 (s, 1H), 4.50-4.46 (m, 1H), 4.25-4.16 (m, 2H), 4.18-4.14 (X part of an AXY system, 1H, $J_{XA}$=6.4 Hz, $J_{XY}$=11.6 Hz), 4.11-4.06 (Y part of an AXY system, 1H, $J_{YA}$=7.6 Hz, $J_{YX}$=11.6 Hz), 3.96 (ad, 1H, $J_{5-6}$=10.0 Hz), 3.75-3.69 (m, 1H), 3.53-3.47 (m 1H), 3.24 (t, 2H, J=7.2 Hz), 3.02-2.98 (A part of an AB system, 1H, $J_{AB}$=13.0 Hz), 2.97-2.94 (B part of an AB system, 1H, $J_{BA}$=13.0 Hz), 2.15 (s, 3H), 2.10 (s, 3H), 2.07 (s, 3H), 2.02 (s, 3H), 2.00 (s, 3H), 1.99-1.98 (m 2H), 1.95 (s, 3H), 1.62-1.56 (m, 4H), 1.43-1.36 (m, 4H). $^{13}$C NMR (50 MHz, $CDCl_3$): δ 170.8, 170.2, 170.1, 169.6, 169.5 (2C), 137.4, 109.0, 95.7, 93.0, 68.6, 68.0, 67.4, 67.3, 66.4, 64.4 (2C), 62.0, 61.7, 51.3, 33.8, 33.6, 29.3, 28.7, 26.4, 25.7, 20.7 (3C), 20.6 (30). $[\alpha]_D^{23}$+22.31 (c 1.09, $CH_2Cl_2$). Elem. Anal. for $C_{32}H_{45}N_3O_{16}S$: Calc. C 50.59, H 5.97, N 5.53. Found: C 50.62, H 6.01, N 5.42; ESI-MS 782.2 [M+Na]$^+$, 798.2 [M+K]$^+$.

Synthesis of Compound 17

To a stirred solution of 20 (120 mg, 0.158 mmol) in CH$_3$OH (3.2 mL), MeONa (2 mg, 0.032 mmol) was added. The mixture was stirred at RT for 2.5 h then the pH adjusted to neutrality with HCl (10% in MeOH). Evaporation of the solvent under vacuum gave a crude which was purified by flash chromatography on silica gel (EtOAc/CH$_3$OH 5:1) to give 17 (72 mg, 90%) as glassy solid. $^1$H NMR (400MHz, CD$_3$OD): δ 4.97 (s, 1H), 4.17-4.12 (m, 1H), 4.09-4.06 (m, 1H), 4.02 (dd, 1H, J$_{4-3}$=3.2 Hz, J$_{4-5}$=1.2 Hz), 3.94 (dd, 1 H, J$_{5-6}$=9.6 Hz, J$_{5-4}$=1.2 Hz), 3.84-3.79 (A part of an ABX$_2$ system, 1 H, J$_{A-B}$=10.0 Hz, J$_{A-X}$=6.4 Hz), 3.77-3.62 (m, 6H), 3.52-3.47 (B part of an ABX$_2$ system, 1H, J$_{B-A}$=10.0 Hz, J$_{B-X}$=6.4 Hz), 3.31-3.28 (m, 2H), 3.05-3.01 (A part of an AB system, 1H, J$_{AB}$=13.0 Hz), 2.99-2.96 (B part of an AB system, 1H, J$_{BA}$=13.0 Hz), 1.94-1.92 (m, 2H), 1.64-1.57 (m, 4H), 1.46-1.41 (m, 4H). $^{13}$C NMR (50 MHz, CD$_3$OD): δ 141.6, 106.4, 96.3, 92.3, 72.6, 70.9, 68.5, 67.8, 66.5, 66.3, 64.6, 62.8, 61.1, 51.1, 36.3, 33.4, 29.2, 28.6, 26.3, 25.6. [α]$_D^{23}$ +51.64 (c 0.25, CH$_3$OH). ESI-MS 530.3 [M+Na]$^+$.

Synthesis of Compound 19

To a stirred solution of 17 (13.2 mg, 0.026 mmol) in a mixture of dry THF (1 mL) and dry DMF (0.1 mL), Ph$_3$P (13.6 mg, 0.052 mmol) and H$_2$O (2.3 μL, 0.13 mmol) were added. The reaction mixture was warmed to 40° C. and stirred for 18 h. Evaporation of the solvent under vacuum gave the crude 4 which was used without purification for the following reaction.

19

To a stirred solution of 4 in dry DMF (1 mL), 18 (50 mg, 0.130 mmol) was added and the reaction mixture was stirred at RT for 6 h. Evaporation of the solvent under vacuum gave a crude which was purified by flash chromatography on silica gel ($CH_2Cl_2/CH_3OH$ 2:1) to give 19 (16.5 mg, 87%) as glassy solid.

$^1$H NMR (400 MHz, $CD_3OD$): δ 8.30-8.29 (AA' part of an AA'MM' system, 2H, $J_{A-M}$=4.8 Hz, Ph), 7.38-7.37 (MM' part of an AA'MM' system, 2H, $J_{M-A}$=4.8 Hz, Ph), 4.96 (s, 1H, $H_a$), 4.15 (adt, 1H, $J_{3-4}$=2.8 Hz, $J_{M-A}$=$J_{3-2'}$=8.8 Hz, $H_3$), 4.09-4.05 (m, 1H, $H_e$), 4.03-4.02 (dd, 1H, $J_{4-3}$=2.8 Hz, $J_{4-5}$=0.8 Hz, $H_4$), 3.94 (dd, 1H, $J_{5-6}$=9.6 Hz, $J_{5-4}$=0.8 Hz, $H_5$), 3.82-3.77 (A part of an $ABX_2$ system, 1H, $J_{A-B}$=10.0 Hz, $J_{A-X}$=6.4 Hz, $H_x$), 3.76-3.61 (m, 6H, $H_d$, $H_6$, $H_7$, $H_{7'}$, $H_f$, $H_{f'}$), 3.51-3.45 (B part of an $ABX_2$ system, 1H, $J_{B-A}$=10.0 Hz, $J_{B-X}$=6.4 Hz, $H_{x'}$), 3.184 (t, 2H, J=7.0 Hz, $CH_{2y}$), 3.03-3.00 (A part of an AB system, 1H, $J_{A-B}$=13.0 Hz, $H_{1'a}$), 2.98-2.95 (B part of an AB system, 1H, $J_{B-A}$=13.0 Hz, $H_{1'b}$), 2.67 (t, 2H, J=7.0 Hz, $CH_2CO$), 2.25 (t, 2H, J=7.0 Hz, $CH_2CO$), 1.93-1.91 (m, 2H, $H_2$, $H_{2'}$), 1.78-1.72 (m, 4H, $CH_2CH_2$), 1.62-1.49 (m, 4H, $CH_2CH_2$), 1.44-1.33 (m, 4H, $CH_2CH_2$). $^{13}$C NMR (50 MHz, $CD_3OD$): δ 174.2, 171.1, 155.7, 141.7, 124.7 (2C), 122.5 (2C), 106.4, 96.3, 92.3, 72.5, 70.8, 68.4, 67.8, 66.4, 66.2, 64.5, 62.7, 60.9, 38.9, 36.1, 35.2, 33.2, 33.1, 29.2, 28.9, 26.3, 25.5, 24.8, 23.8. Elem. Anal. for $C_{32}H_{46}N_2O_{15}S$: Calc. C 52.59, H 6.34, N 3.83. Found: C 52.79, H 6.61, N 5.51; ESI-MS 753.3 $[M+Na]^+$.

Synthesis of Compound 5

19

Buffer pH 7.2

5

To a solution of KLH (20 mg) in 20 mL of buffer (0.1 M sodium phosphate and 0.15 M sodium chloride, pH 7.2) 19 (15 mg, 0.020 mmol) was added and the mixture was stirred overnight at RT. The solution was lyophilized and the solid was dialysed to give 18.5 mg of glycoconjugate 5.

Thioether-protein ratios were evaluated by determination of free lysine amino groups before and after conjugation by titration with trinitrobenzensulfonic acid.

Immunization and Fusion.

Two Female, 8 weeks old, BALB/c mice (Ce.S.A.L., Firenze) were immunized with intraperitoneal (mouse A) and intravenous (mouse B) injections with antigen-KLH conjugate solution four times, twice a week. In the first immunization the antigen was injected as a 1:1 (v/v) emulsion in Freund's complete adjuvant (mouse A) to a final volume of 0.2 mL and as a 1:1 (v/v) solution in sterile PBS (mouse B) to a total volume of 0.2 mL. The second and third immunizations were performed in the way, except that an incomplete Freund's adjuvant was used in mouse A. The final immunization was given 3 days prior to cell fusion, through intravenous injection in both mouse A and B. On the day of fusion mice were killed by cervical dislocation, spleens were harvested, and $1 \times 10^8$ cells were collected and used for each fusion. Spleen cells were fused with a hypoxanthine-aminopterin-thymidine (HAT) sensitive mouse myeloma cell line, NSO, by the polyethylene glycol (PEG) method (29). NS0 cells were maintained in DMEM with 10% Fetalclone I (HyClone) and split 1:2 the day before fusion. $1 \times 10^8$ NS0 cells were mixed in serum-free DMEM, centrifuged and, after removing the supernatant, were placed in a water bath at 37° C. and 1 mL of pre-warmed PEG (Sigma-Aldrich) were added, "drop to drop". At the end of PEG addition, pre-warmed serum-free medium was added and the tube was centrifuged to remove supernatant. The fusion product was resuspended in DMEM containing 20% Fetalclone I and 1× HAT, and the ensuing cell suspension was plated in 24 well plates; cells were incubated at 37° C. in a $CO_2$ incubator.

ELISA Tests

Hybridoma supernatants were screened for binding to $GM_3$ ganglioside by enzyme-linked immunosorbent assay (ELISA). The ELISA 96 well plate (Corning) was first treated with 100 µL of $GM_3$ (30 µg/mL in 100% ethanol) overnight at room temperature. To minimize nonspecific adsorption 300 µL of PBS containing 0.05% Tween (TPBS) and 3% BSA were added for 1 h, and washed three times with TPBS. Hybridoma culture supernatants (100 µL/well) were added to the coated plate and incubated at room temperature for 2 h. Subsequently, the plate was washed and incubated with secondary antibody (peroxidase-labeled anti-mouse, 1:500 in TPBS) for 1 h. The plate was washed three times with TPBS, then 100 µL tetramethylbenzidine (TMB, Sigma) were added to each well. The plate was further incubated for 5 min, and hence the reaction was stopped with HCl 0.5 M. Absorbance was measured using a microplate reader (ELX800, Bio-Tek Instruments, Inc.) at 450 nm.

Immunocitochemistry (ICC)

ICC was performed on B16F1 melanoma. Cultured B16 melanoma cells were grown in DMEM supplemented with 10% FCS and 2 mM L-glutamine. Cells were mounted on polylysine-coated slides and fixed with formaline solution. After blocking endogenous peroxidases, cells were treated with proteinase K (Roche; 5 g/ml in PBS) and UltraVBlock solution (LabVision) and then incubated with the primary antibody (hybridomas supernatant) and with the anti-GM3 antibody (M2590) diluted 1:100 in PBS-UltraVBlock (10:1 v/v) overnight at 4° C. Immunostaining was carried out using a commercially available kit (PicTure Plus kit; Zymed). For the negative control hybridomas medium replacing the primary antibody was used.

What is claimed is:

1. A specific antibody against a compound of formula (I)

wherein
  X is O, NH, S, or $CH_2$;
  L is a linker that is a divalent spacer;
  A is an adjuvant or carrier that is an immunogenic molecule or an immunogenic particle; and
  wherein bonds between linker and saccharide moiety and between linker and carrier are of covalent type;
  wherein the linker L presents a chemical structure suitable to space the saccharide moiety and the carrier by 7-30 atoms when the adjuvant/carrier A is a biomacromolecule or by 19-30 atoms when the adjuvant/carrier A is a metallic nanoparticle; and
  wherein said carrier/adjuvant A is selected from the group consisting of a macromolecule, a macrocycle, a dendrimer, a liposome, a nanoparticle, an oligosaccharide featuring from two to five monosaccharidic units and dendritic cells.

2. The antibody according to claim 1 obtainable by immunization of experimental animal of murine genus by administration of said compound of formula (I).

3. A method comprising administering an antibody according to claim 1 as a medicament to a patient in need thereof.

4. A method comprising administering an antibody according to claim 1 to a patient in need of treatment and/or prevention of tumors whose cells hyper-express GM-3 ganglioside and/or GM-3 lactone.

5. A method comprising the use of an antibodies according to claim 1 as a tool for diagnosis and/or prognosis of tumors whose cells hyper-express GM-3 ganglioside and/or GM-3 lactone.

6. A pharmaceutical composition containing at least an antibody according to claim 1 and at least another pharmaceutically acceptable ingredient.

* * * * *